United States Patent [19]
Ovil

[11] Patent Number: 5,871,489
[45] Date of Patent: Feb. 16, 1999

[54] SURGICAL IMPLEMENT PARTICULARLY USEFUL FOR IMPLANTING PROSTHETIC HEART VALVES, VALVE HOLDER PARTICULARLY USEFUL THEREWITH AND SURGICAL METHOD INCLUDING SUCH IMPLEMENT

[75] Inventor: Joel Ovil, Ramat Hasharon, Israel

[73] Assignee: S.M.T. (Medical Technologies) Ltd, Tel-Aviv, Israel

[21] Appl. No.: 712,680

[22] Filed: Sep. 13, 1996

Related U.S. Application Data

[63] Continuation-in-part of Ser. No. 640,149, Apr. 3, 1996, Pat. No. 5,690,654.

[30] Foreign Application Priority Data

Jan. 24, 1996 [IL] Israel ......................................... 116891

[51] Int. Cl.⁶ .................................................. A61B 17/04
[52] U.S. Cl. ............................. 606/148; 606/139; 623/2; 623/900
[58] Field of Search .................................... 606/148, 139; 623/2, 900

[56] References Cited

U.S. PATENT DOCUMENTS

| | | |
|---|---|---|
| 2,588,589 | 3/1952 | Tauber . |
| 2,692,599 | 10/1954 | Creelman . |
| 4,185,636 | 1/1980 | Gabbay et al. . |
| 4,492,229 | 1/1985 | Grunwald . |
| 4,702,250 | 10/1987 | Ovil et al. . |
| 4,932,965 | 6/1990 | Phillips . |
| 5,207,703 | 5/1993 | Jain . |
| 5,304,184 | 4/1994 | Hathaway et al. . |
| 5,306,296 | 4/1994 | Wright et al. . |
| 5,439,467 | 8/1995 | Benderev et al. . |
| 5,443,502 | 8/1995 | Caudillo et al. . |
| 5,569,300 | 10/1996 | Redmon . |

FOREIGN PATENT DOCUMENTS

| | | |
|---|---|---|
| 1736446 | 5/1992 | U.S.S.R. . |
| 2181950 | 5/1987 | United Kingdom . |
| WO93/01768 | 4/1993 | WIPO ......................................... 623/2 |

Primary Examiner—Michael Buiz
Assistant Examiner—Tina T. D. Pham
Attorney, Agent, or Firm—Benjamin J. Barish

[57] ABSTRACT

A surgical implement particularly useful for implanting a prosthetic valve in an excised annulus includes a manually grippable handle, and a suture retainer carried by the handle and having an outer face carrying a coiled spring whose coils define an annular array of slits each having opposed yielding surfaces for receiving and releasably retaining sutures between selected coils. Optimum spacing of the sutures according to the shape of the excised annulus is attained by providing reference ribs between selected coils of the spring, and also by making the outer annular face of the suture retainer of substantially the same shape as that of the excised annulus. Implements are described, with a suture retainer and without a suture retainer, including an illuminating device for artificially illuminating the working area. Also described is a method of implanting a prosthetic valve in a quick and efficient manner using such implements.

8 Claims, 11 Drawing Sheets

SURGICAL IMPLEMENT PARTICULARLY USEFUL FOR IMPLANTING PROSTHETIC HEART VALVES, VALVE HOLDER PARTICULARLY USEFUL THEREWITH AND SURGICAL METHOD INCLUDING SUCH IMPLEMENT

RELATED PATENT APPLICATION

The present application is a continuation-in-part of patent application Ser. No. 08/640,149 filed Apr. 30, 1996, now U.S. Pat. No. 5,690,654.

FIELD AND BACKGROUND OF THE INVENTION

The present invention relates to a surgical implement particularly useful for implanting a prosthetic device in an excised annulus. The invention is especially useful for implanting a prosthetic heart valve, and is therefore described below with respect to such an application. The invention also relates to a novel valve holder particularly useful with the above surgical implement. The invention also relates to a surgical method for implanting prosthetic devices, particularly heart valves.

The surgical replacement of a defective heart valve has become a widely practiced surgical operation. In such a surgical operation, the defecting valve is surgically removed, and a bio or mechanical prosthetic valve is implanted in the excised annulus by a plurality of sutures, usually varying from 12–20, depending upon the size of the excised annulus. Such a surgical operation involves cardiopulmonary bypass circulation and cardiac arrest. The longer the period of cardiac arrest, the greater the danger of post-operative complications. Many implements have been proposed for use in such a surgical operation in order to shorten the period of cardiac arrest. Examples of the known devices are described in U.S. Pat. Nos. 4,185,636, 4,492,229, 4,932,965, and U.S. Pat. No. 4,702,250 of which I am a joint inventor. However, insofar as I am aware, none of these previously known devices has found widespread use.

OBJECTS AND BRIEF SUMMARY OF THE INVENTION

An object of the present invention is to provide a novel surgical implement particularly useful for implanting a prosthetic device, especially a prosthetic heart valve, having advantages over the previously known implements including that of the above-cited U.S. Pat. No. 4,702,250, as will be described more particularly below. Another object of the invention is to provide a valve holder of a novel construction particularly, but not exclusively, useful with the above novel surgical implement. Another object of the invention is to provide a novel surgical method for implanting prosthetic devices especially valves.

According to one aspect of the invention in this application, there is provided a surgical implement particularly useful for implanting a prosthetic device in a working area, comprising: a manually grippable handle; a holder carried by the handle for holding a prosthetic device; and an illuminator carried by the handle for projecting artificial light into the working area while the holder holds the prosthetic device. The illuminator includes a light conductor carried by the handle and has one end for receiving light from an external light source, the opposite end of the light conductor passing through the holder for conducting light from the light source to the working area.

The invention is particularly useful, and is therefore described below with respect to, an implement wherein the prosthetic device is a prosthetic valve having a valve member pivotal to an open position or to a closed position, and wherein the holder is a valve holder which releasably holds the prosthetic valve with its valve member pivotted in the open position to permit light from the light conductor to pass through the valve holder and the prosthetic valve held thereby and to illuminate the working area.

According to a still further aspect of the invention, there is provided a valve holder for holding a prosthetic valve having a sewing ring for implanting the valve in a working area, and a pivotal valve member pivotal to open and closed positions; the valve holder including an attaching section for attaching the valve holder to a manipulatable surgical implement, and a releasble holding section for releasably holding the prosthetic valve; the valve holder being formed with a bore extending through the attaching section and dimensioned to receive a light conductor from the surgical implement and to space the tip of the light conductor from the pivotal valve member; the releasable holding device holding the prosthetic valve with the valve member in its open position to permit light from the light conductor to pass through the valve holder and the prosthetic valve held thereby to illuminate the working area.

Several embodiments of the invention are described with respect to different types of prosthetic valves now commercially available with their respective valve holders.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
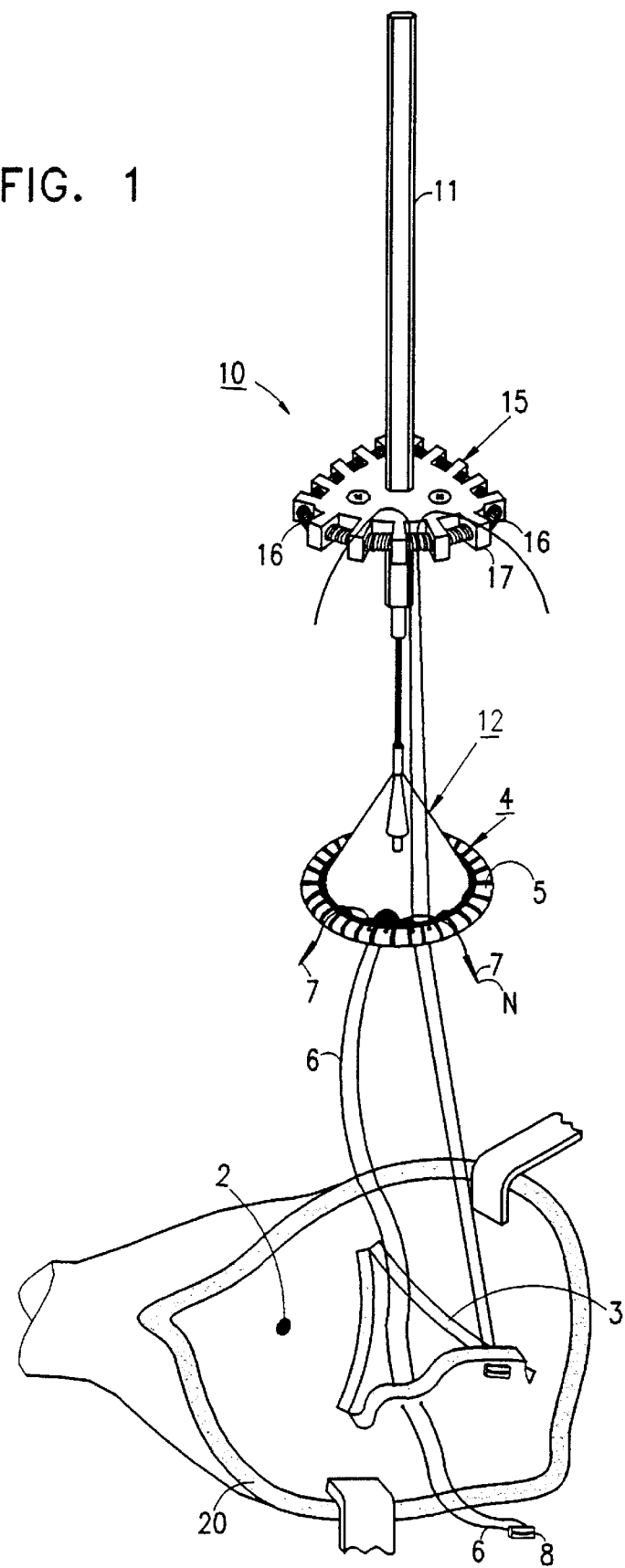
FIG. 1 is a three-dimensional view illustrating of one form of surgical implement constructed in accordance with the present invention.

The surgical implements illustrated in the drawings are for implanting a prosthetic aortic or pulmonic valve, which involves making an excised annulus of generally curved triangular shape. Thus, FIG. 1 pictorially illustrates at 2 the site of the diseased valve to be replaced, at 3 the excised annulus of curved triangular configuration prepared by the surgeon after removing the defective valve and preparing the site for implanting the prosthetic valve, and at 4 the prosthetic valve to be implanted in the excised annulus 3. Such a valve is normally provided with a sewing ring 5 for receiving the sutures 6 used in implanting the prosthetic valve in the excised annulus 3.

As will be described more particularly below, each suture 6 is a double-armed suture; that is, it carries a needle 7 at each of its two opposite ends for passing through tissue at the excised annulus 3 and through the sewing ring 5 of the prosthetic valve 4. Each suture is also provided with a pledget 8, e.g., of "Teflon" (Reg.T.M.), in order to increase the surface contact between the suture and the tissue receiving it at the excised annulus.

The surgical implement illustrated in FIG. 1 is generally designated 10. It includes a manually grippable handle 11 and a valve holder 12 for releasably holding the prosthetic valve 4. Any known type of valve holder may be used for this purpose, for example as described in the above-cited U.S. Pat. No. 4,702,250. However, when the implement is to be used with illumination as described below, the valve holder is preferably one of the constructions described below for the respective type of prosthetic valve now commercially available.

The surgical implement in FIG. 1 further includes a suture retainer, generally designated 15, carried by the handle 11 preferably at the distal part of the handle close to the prosthetic valve. A coiled spring 16 is supported around the outer annular face of the suture retainer 15, for receiving and releasably retaining the sutures 16 between selected coils of the spring. For this purpose, suture retainer 12 is integrally formed with a plurality of spaced ribs 17 having openings 18 (FIG. 2) for receiving the coiled spring 16.

Figure 2:
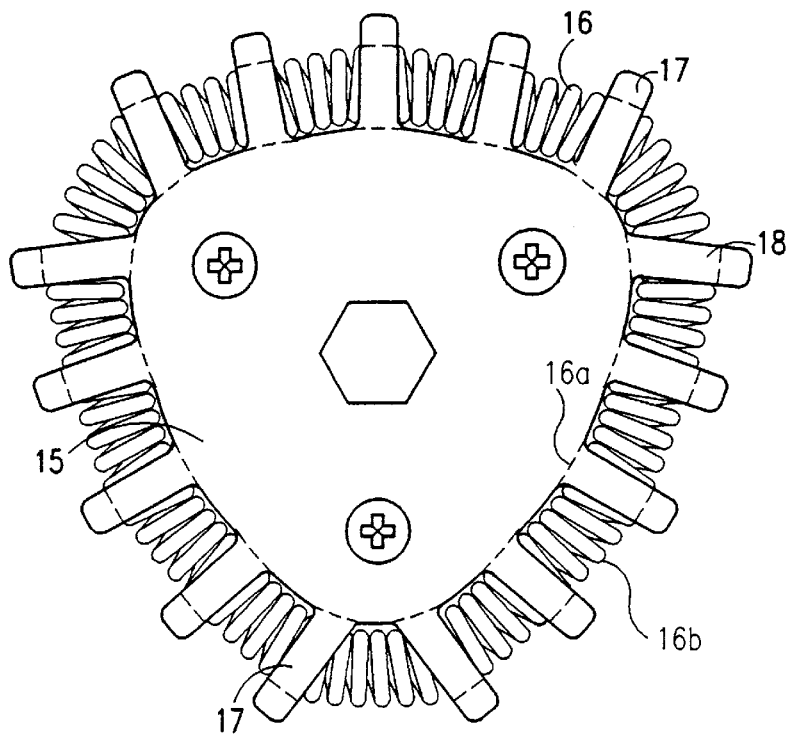
FIG. 2 is a top plan view illustrating the suture retainer in the implement of FIG. 1.

The coiled spring 16, as shown in FIG. 2, is made of wire of circular cross-section coiled into a helix and supported in an annular configuration around the outer annular face of the suture retainer 15. The coiled spring is applied under light traction so that when supported in the illustrated curved configuration, the coils are lightly pressed together in the inner face 16a of the spring, and tend to spread apart slighly in the outer face 16b. The coiled spring thus forms an annular array of slits having opposed, yielding surfaces for receiving and releasably retaining the sutures. The circular cross-section of the wire used for making the coiled spring results in the outer surfaces defining the slits diverging in the outward direction, thereby facilitating the insertion of the sutures between the coils.

As described earlier, the outer shape of suture retainer 15 is generally the same as the excised annulus 3 prepared by the surgeon for implanting the prosthetic valve 4. In the example illustrated in FIGS. 1 and 2, the defective valve to be replaced is an aortic valve, which involves excising an annulus 3 of generally curved triangular configuration. Therefore the configuration of the surgical suture retainer 15 is also of generally the same curved triangular shape as the excised annulus 3.

The ribs 17, besides holding the coiled spring 16 in an annular configuration on the outer face of the suture retainer 15, also serve as visually discernible dividers dividing the outer annular face of the suture retainer into a plurality of divisions, one for each of the sutures to be applied. For example, in the prosthetic valve illustrated in FIG. 1, normally fifteen sutures would be used, and therefore there would be fifteen ribs 17 dividing the outer surface of the suture retainer into fifteen divisions, one for receiving each of the fifteen sutures. Each of the fifteen divisions defined by the ribs 17 accommodates at least two (preferably three) coils of the coiled spring 16, defining at least two suture-receiving slits, to facilitate receiving, identifying, and tying the two opposite ends of the suture to be received in the respective division. Preferably, however, there are more than three coils, e.g., four or five coils, in each division. This facilitates the application of the sutures by the surgeon without requiring the surgeon to aim the suture in a precise location in the respective division of the suture holder. It also gives the surgeon the option of adding an additional suture or two at any location of the excised annulus should this appear to be necessary or desirable during the course of the surgical operation.

While the suture retainer 15 is of generally the same external shape as the excised annulus 3, it is may be of larger size to facilitate handling and proper placement of the sutures in their respective locations. The suture retainer 15 may also be of smaller size, and/or may be of transparent plastic, to minimize obstruction with the surgical site.

The surgical implement illustrated in FIGS. 1 and 2 may be used in the following manner for replacing a defecting aortic valve.

The chest is opened by a midsternotomy, and a cardiopulmonary bypass is established by cannulation of the aortic root and the right atrium. The aorta is then crossclamped, and cardioplegia is injected in order to arrest the heart. The aortic root is opened via an S-shaped incision, the defective aortic valve is excised, and an excised annulus 3 of generally curved triangular configuration is prepared for receiving the prosthetic valve 4.

The surgical implement 10 is preloaded with the prosthetic valve 4 but not with the sutures 6 to be used in the implanting. Rather, the implement is equipped with a suture retainer 15 of appropriate configuration (in this, of case curved triangular configuration) coresponding to the excised annulus 3 to receive the prosthetic valve. Each of the sutures 6 carries a needle 7 at each of its two opposite ends, and a pledget 8 at the location, or slidable to the location, of contact of the suture with the tissue around the excised annulus.

The stitching is started by passing the needle 7 at one end of the first suture 6 through the non-coronary cusp rim 20 and then through the sewing ring 5 of the prosthetic valve 4. That end of the suture is then inserted between a pair of coils of the spring 16 at the division allocated to that suture between the ribs 17. The suture is slightly tensioned, and is releasably retained under this tension by the coils of the spring. The needle is then cut away from the respective end of the suture leaving an excess of the suture at that end.

The opposite end of the same suture is then applied in the same manner and is inserted between a pair of coils adjacent to the one receiving the first-mentioned end in the same division defined by the ribs 17. The needle at that end is also cut away leaving an excess of the suture at that end.

The coils of spring 16 releasably retain both ends of the suture such that handle 11 may be pulled slightly outwardly to apply a tension to the two suture ends and also to pull out slightly the tissue engaged by the suture. The pledget 8 of the respective suture provides a large surface are of contact between the suture and the tissue, thereby permitting this tension while decreasing the possibility of tearing the tissue. If excess tension is applied to the sutures, this excess tention will be taken-up by the sliding of the sutures between the coils of the spring, thereby minimizing the risk of tearing the annulus tissue.

The other sutures 6 are then applied in the same manner, one after the other, according to the mattress techniques, i.e., from the outside to the inside. They are received between adjacent coils of the spring 16 in their respective divisions defined by the ribs 17 of the suture retainer 15, according to their respective locations in the excised annulus.

After all the sutures have thus been applied and their needles cut-away, handle 11 may then be moved slightly outwardly to tension all the sutures and to better expose the excised annulus. If any suture is found to be insufficiently tensioned, this can be easily corrected by merely pulling on the respective suture to apply the proper tension to it. As mentioned earlier, if excessive tension is applied to one or more of the sutures, the respective suture will merely slip between the coils of the spring, thereby reducing the risk of tearing the annulus tissue.

After the sutures have thus been applied to the excised annulus and tensioned to better expose the annulus, the prosthetic valve 4 is released from holder 12 in the manner described below, and is slid into place into the annulus. Each pair of sutures are then tied down and cut. The aortic opening is then sutured, and the aortic clamp is released to allow the heart to resume beating.

The use of the surgical implement illustrated in FIGS. 1 and 2 thus enables a number of important advantages to be gained, as compared to the existing techniques: Thus, the novel implement enables the surgeon to select the type of suture to be used, something not permitted by pre-loading suture retainers. It also allows simultaneous suturing of the excised annulus and the valve sewing ring even when using pledgeted double-armed sutures in the mattress fashion, by far the most popular technique in present use, while minimizing wasted time caused by needle search. This enables the cardiac arrest time to be substantially reduced as compared to the present techniques using pledgeted double-armed sutures in which the excised annulus and the sewing ring are sutured separately.

The above-described implement and procedure also provide better exposure and better division of the suture site to the surgeon. It also allows suture-length adjustment, reduces the danger of annular tears, retains the sutures without looping or tying, and decreases the possibility of entanglements and loose ends of the sutures as they are applied. Further, forming the annular surface of the suture retainer generally of the same configuration as the excised annulus, and dividing this annular surface into divisions according to the sutures to be applied, greatly facilitates the application of each suture to its proper location without the surgeon having to precisely aim each suture. In addition, providing each division with at least two slits aids the application, identification and tying of the opposite ends of each suture; while providing more than two slits at each division permits the surgeon to add a suture at any particular location should this appear to be necessary or desirable during the course of the operation.

All the foregoing advantages are extremely important in reducing post-operative mortality and morbidity and particularly the danger of the often-fatal post-operative paravulvular leak.

Figure 3:
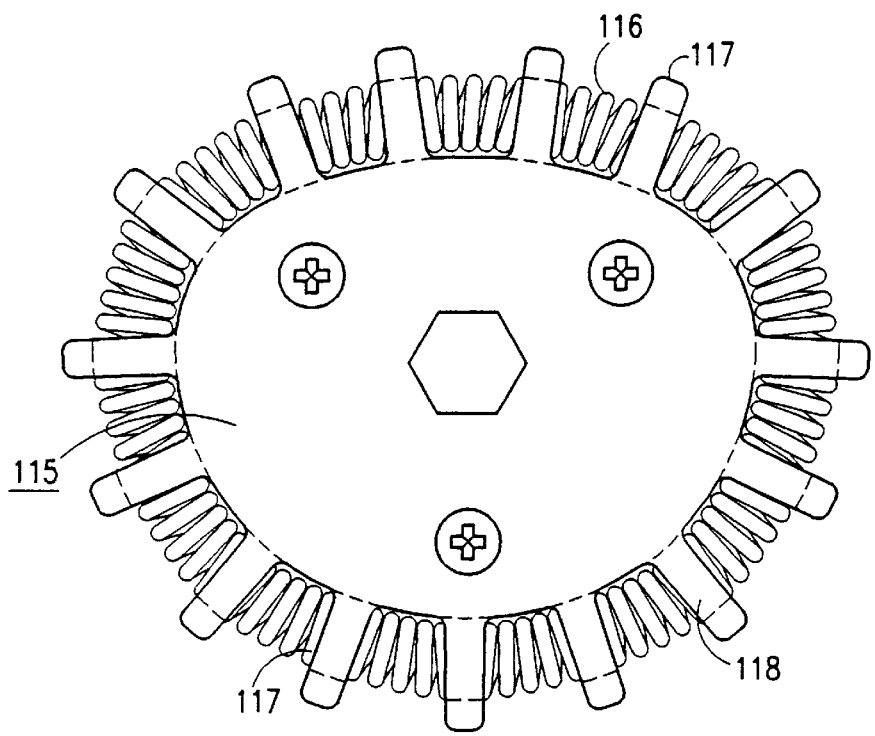
FIG. 3 is a top plan view of another type of suture retainer that may be included in the surgical implement of FIG. 1.

FIG. 3 illustrates a suture retainer for use in implanting a prosthetic valve requiring an excised annulus of a curved oval shape, such as when implanting a mitral valve or a tricuspid valve. In this case, the suture retainer, therein designated 115, would be of the same curved oval shape as the excised annulus to be prepared for the respective valve. It could be of slightly larger size to facilitate handling of the sutures, or of slightly smaller size, and preferably transparent, to reduce obstruction of the surgical site. In all other respects, the suture retainer illustrated in FIG. 3 would be incorporated in the surgical implement illustrated in FIG. 1 and would be used in the same manner as described above for implanting the prosthetic valve.

Figure 4:
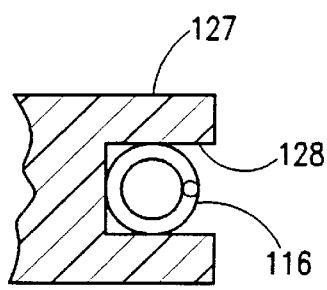
FIG. 4 is a partial sectional view illustrating a modification in the construction of the suture retainer of either FIGS. 1 or 2.

In the suture retainer 115 illustrated in FIG. 3 (as well as that illustrated in FIGS. 1 and 2), the coiled spring 116 is retained in an annular configuration around the outer face of the suture retainer by being passed through holes 118 in the ribs 117 integrally formed in the suture retainer. FIG. 4 illustrates a variation wherein the ribs, therein designated 127, are provided with edge slots 128 for retaining the coiled spring in its annular configuration around the outer face of the suture retainer. Thus, the coiled spring may be formed in an endless loop and simply applied via the edge slot 128 in the ribs 127.

The use of an annularly-deployed coiled spring applied around an annular suture retainer formed with ribs as described above has been found to be particularly advantageous since such a construction defines an annular array of slits having suture-reference markings for receiving and releasably retaining the sutures. However, other suture retainer constructions could be used having these characteristics, such as a plastic disc or an annular tube or rod formed with a plurality of radially-extending slits progressing inwardly from its outer edge.

Also, while it is preferred to form the suture retainer with an outer annular face generally of the same shape as that of the excised annulus in order to facilitate optimum spacing of the sutures with respect to the excised annulus, other arrangements could be used for providing a visually discernible representation of the shape of the excised annulus. For example, the shape of the excised annulus could be drawn on the suture retainer, which may therefore be of another shape (e.g., circular shape) to facilitate optimum spacing of the sutures with respect to the excised annulus. Also, the visually discernible dividers of the outer annular surface of the suture retainer could be merely in the form of markings applied to the suture retainer, rather than ribs integrally formed with the suture retainer.

Figure 5:
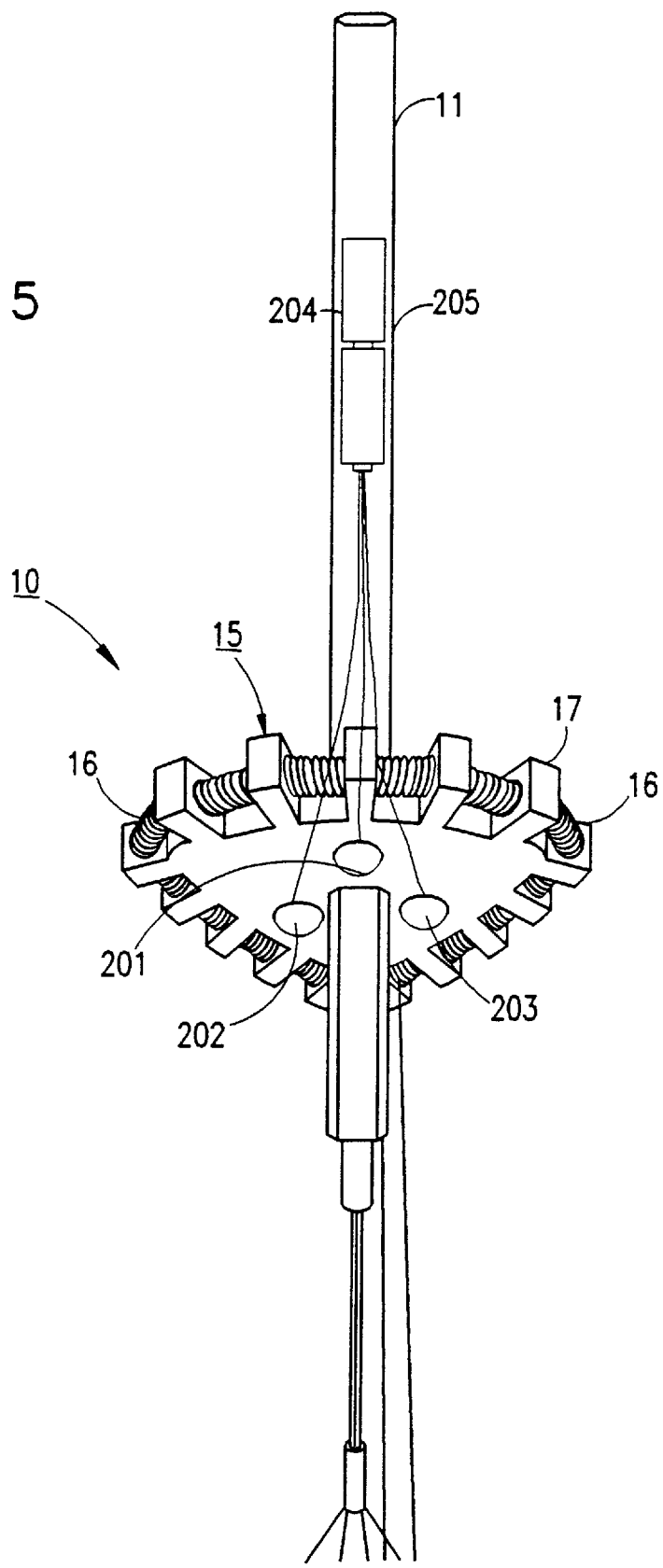
FIG. 5 illustrates another embodiment of the invention including an artificial illuminator.
Figure 6:
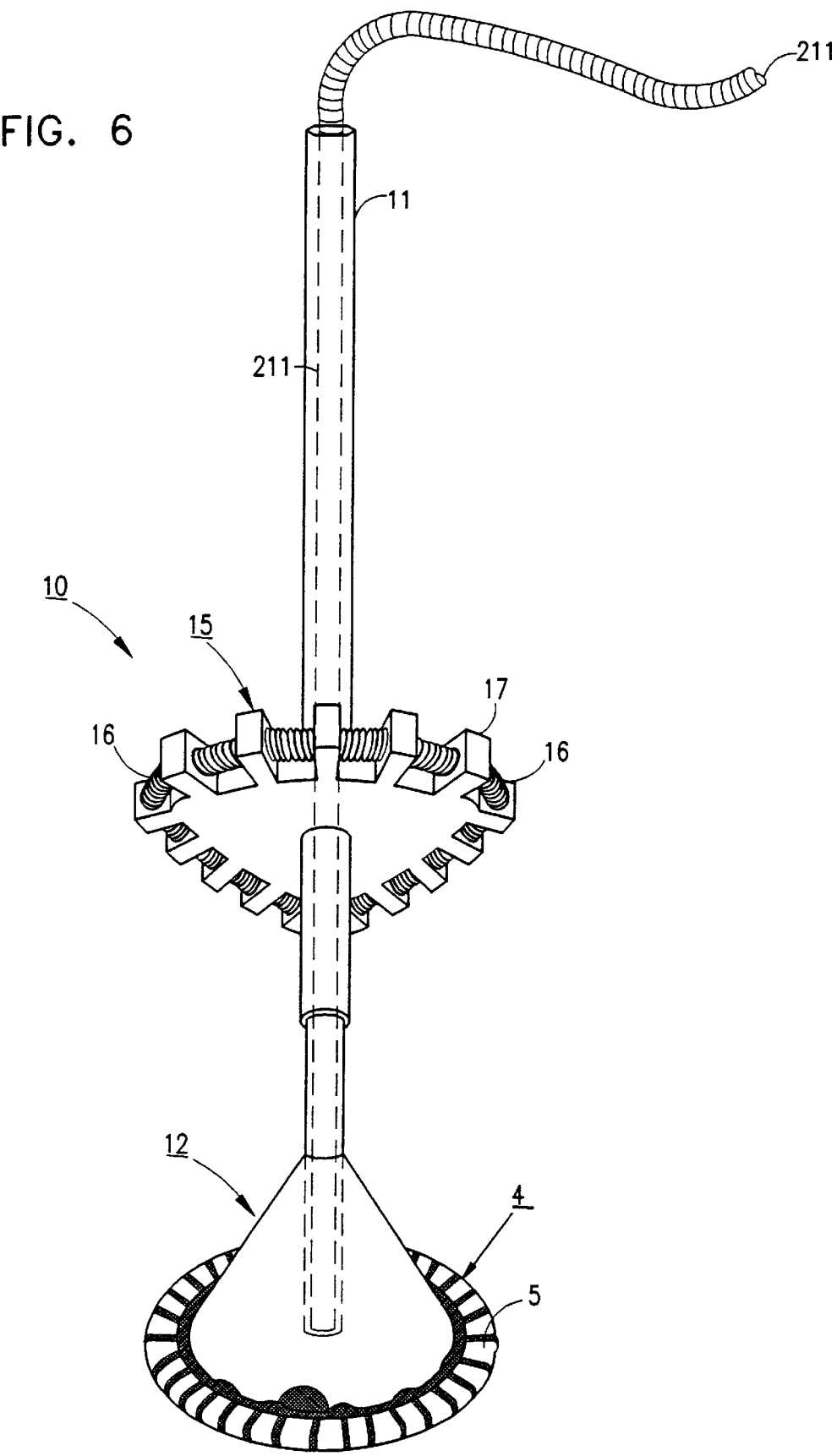
FIG. 6 illustrates a still further embodiment of the invention illustrating another type of illuminator which may be used.

FIGS. 5 and 6 illustrate implements similar to that of FIG. 1, but including an artificial illuminator for illuminating the working area. To faciliate understanding, the same reference numerals have been used in these figures as in FIG. 1 to identify corresponding elements. In the implement of FIG.

5, the suture retainer 15 is provided with three light soures 201, 202, 203 (e.g., LEDs), energized by batteries 204 within a battery compartment 205 in the handle 11, for illuminating the working area at the underside of the suture retainer. In FIG. 6, the artificial illuminator includes a light conductor in the form of an optical fiber bundle 211 within the handle 11 optically coupleable at one end to a light box (not shown), such as provided for the regular pediatric bronchoscope commonly available in operating rooms, and extending through the valve-holder 12 for the prosthetic valve 4 to illuminate the working area.

Figure 7:
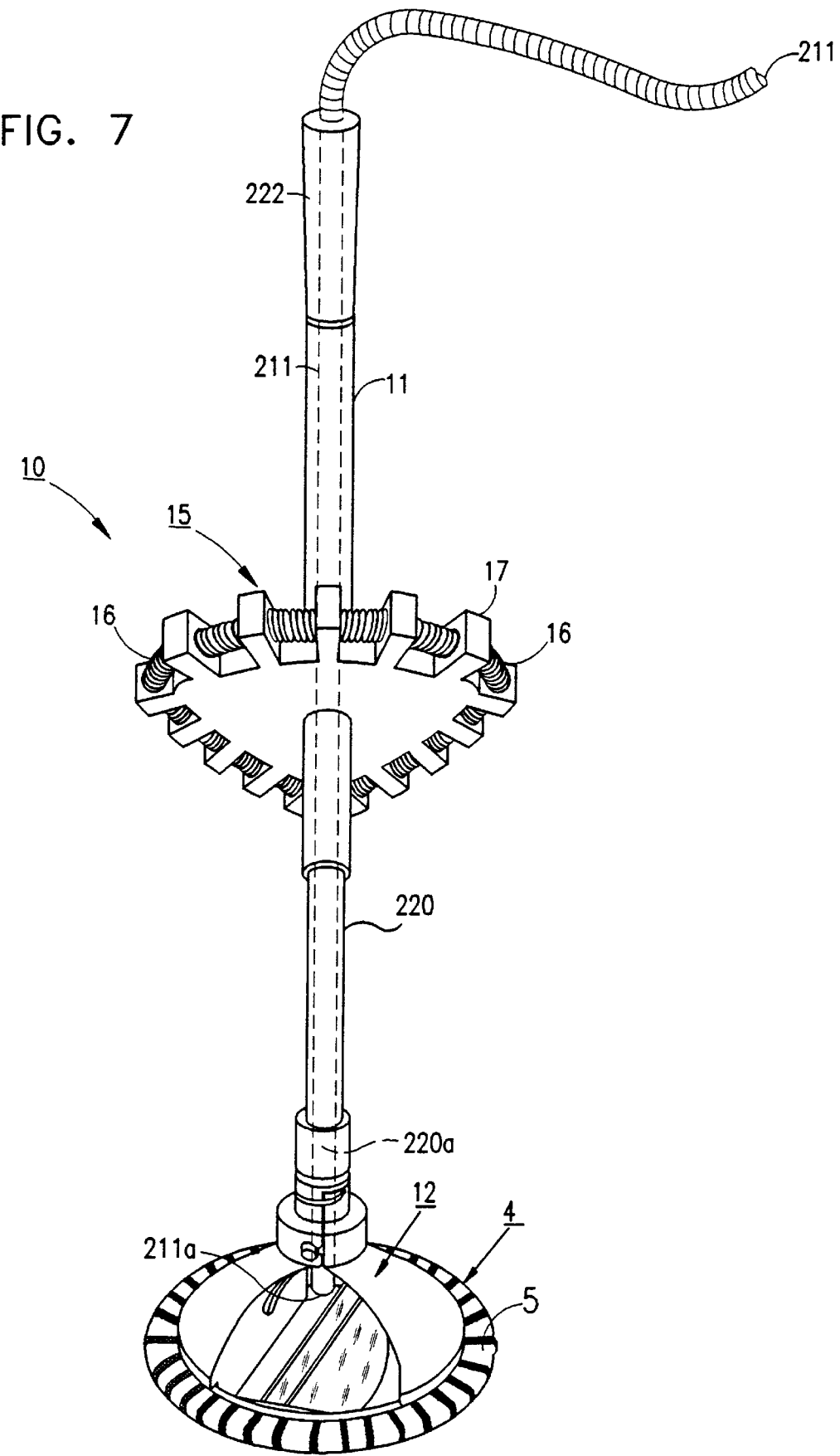
FIG. 7 illustrates another implement similar to that of FIG. 6 including a valve holder for one known type of prosthetic valve.

FIG. 7 illustrates an implement similar to that of FIG. 6 equipped with an artificial illuminator including a light conductor in the form of an optical fiber 211 extending through the handle 11. FIG. 7 also illustrates a particular construction of the valve holder 12, as described below with reference to FIGS. 8–10. An end section 220 of the handle between the handle 11 and the valve holder 12, is formed with external threads 220a for threadedly receiving the valve holder 12.

The optical fiber 211, serving as the light conductor for conducting the light to illuminate the working area, passes through aligned bores in handle 11, its end section 220, and valve holder 12 carried by the latter section. The end of optical fiber 211 terminates within the valve holder 12 but is spaced above the prosthetic valve 4 held by the holder so as not to interfere with the leaflet valve members of the prosthetic valve 4, as described more particularly below with reference to FIGS. 8–11. In order to precisely locate the tip 211a of optical fiber 211 with respect to valve holder 12, an annular collar 222 is fixed to the optical fiber 211 such as to be engageable with the outer end of handle 11, and thereby to limit the position of the tip 211a of the optical fiber with respect to the valve holder 12.

FIGS. 8–11 illustrate a novel construction of valve holder 12 which may be used with the implement of FIG. 7, as well as the other implements described herein. Valve holder 12 illustrated in FIGS. 8–11 is similar to a known construction, e.g., as described in U.S. Pat. No. 5,443,502, but includes a number of modifications to enable the valve holder to be used with respect to one well known type of prosthetic valve and to accommodate the light conductor of the illuminator for illuminating the working area.

Figure 10:
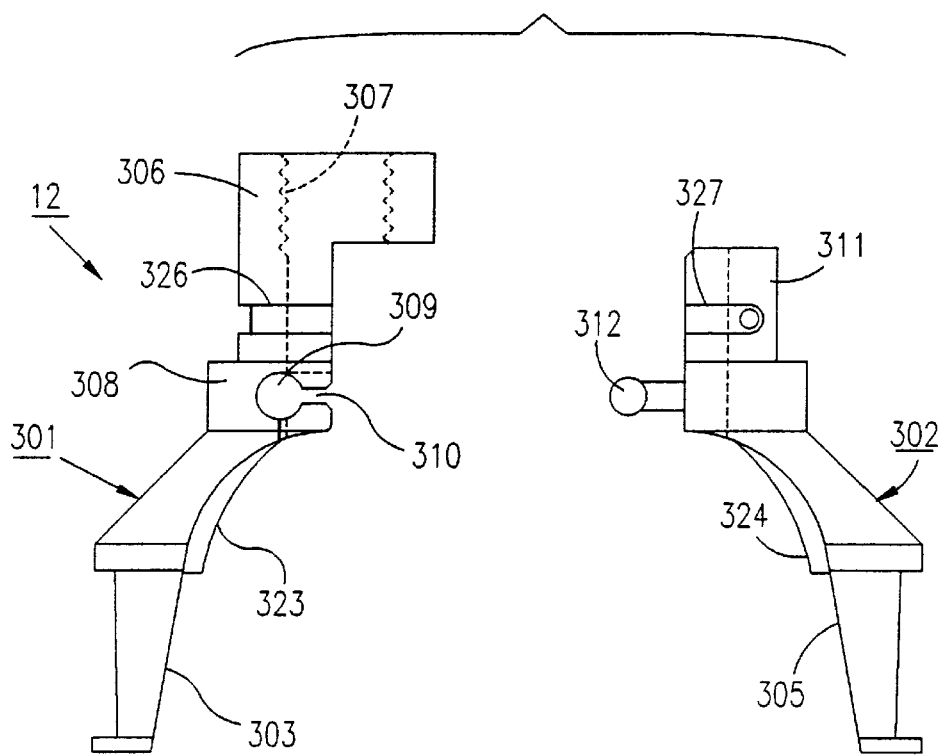
FIGS. 10 and 11 are exploded side and top views, respectively, illustrating two parts of the valve holder of FIGS. 8 and 9.
Figure 11:
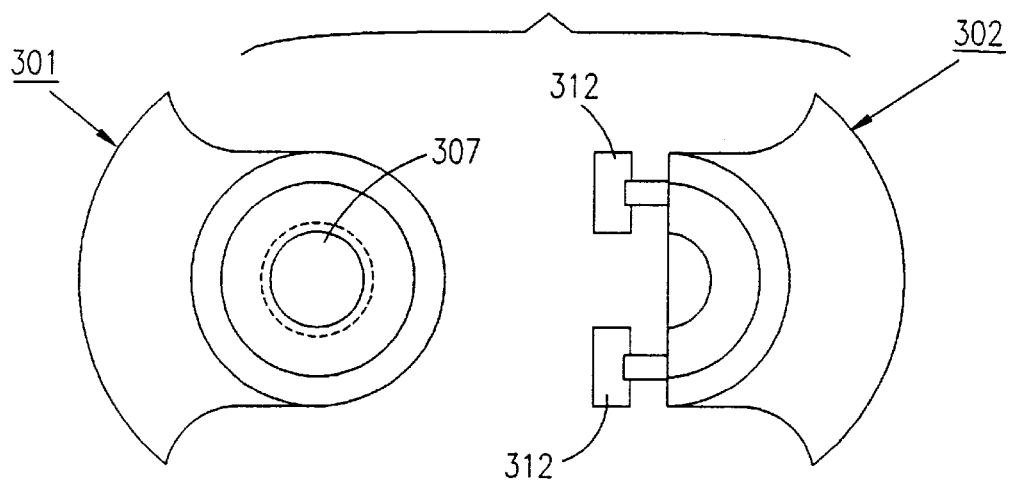

As shown particularly in FIGS. 10 and 11, valve holder 12 is constituted of two pivotal parts 301, 302, each formed at its lower end with an arm 303, 305. Part 301 further includes, at its upper end, a collar 306 formed with an internally-threaded socket 307 for threadedly receiving the externally-threaded end 220a (FIG. 7) of the intermediate handle section 220.

Cylindrical collar 306 at one end of pivotal part 301 is joined to arm 303 by an intermediate section 308 of semi-cylindrical configuration and formed at its opposite sides with a pair of aligned cylindrical bores 309 communicating with the outer surface of the section by a pair of slots 310. Pivotal part 302 includes a section 311 at one end, of similar semi-cylindrical configuration complementary to the intermediate section 308 of pivotal part 301. Pivotal part 302 also includes a pair of cylindrical trunnions 312 integrally formed with the intermediate section 311. These trunnions are receivable via slots 310 into the cylindrical bores 309 of intermediate section 308 of pivotal part 301.

Figure 8:
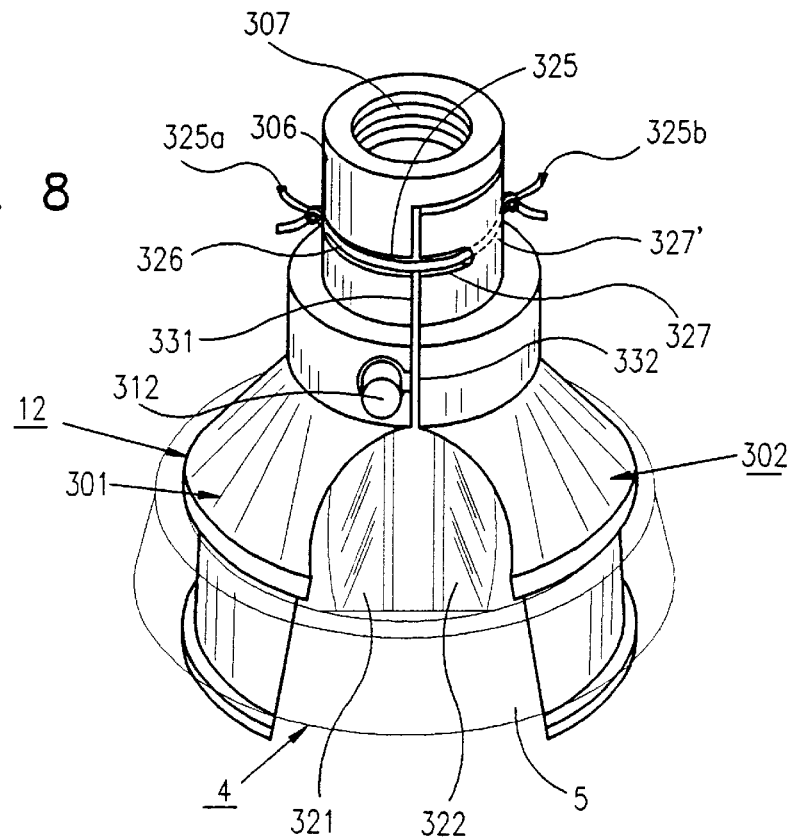
FIG. 8 is a three-dimensional view of the valve holder of FIG. 7.
Figure 9:
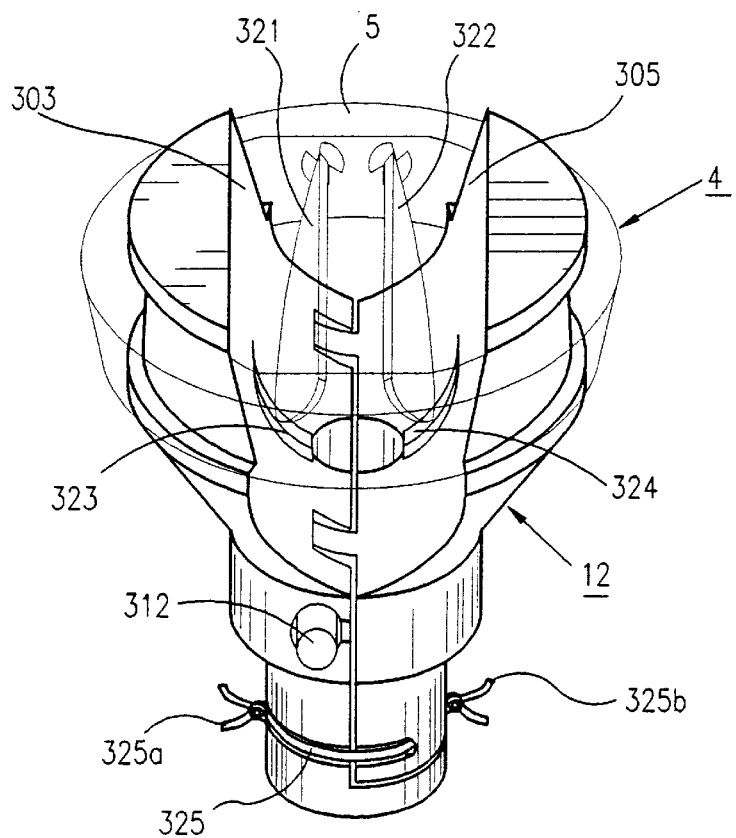
FIG. 9 is a three-dimensional view of the valve holder of FIG. 8 but as seen from the bottom of the valve holder.

The arrangement is such that when trunnions 312 are received within bores 309, the pair of arms 303, 305 are pivotally mounted together at their upper ends to assume either an operative position, as shown in FIGS. 8 and 9 for holding the prosthetic valve 4, or to a collapsed position for releasing the prosthetic valve. Prosthetic valve 4 may be of a conventional construction including a sewing ring 5, as previously described, and a pair of pivotal leaflet valve members 321, 322. When the prosthetic valve 4 is applied to the valve holder, the pivotal arms 303, 305 of the valve holder are received within the leaflets 321, 322 to pivot the two leaflets to their open positions, so as to permit the light from optic fiber 211 to pass through the valve and to illuminate the working area.

In the mitral position, the two leaflets 321, 322 tend to open by gravity. However, in the aortic position, the two leaflets tend to close by gravity.

To better assure that the two pivotal arms 303, 305 pivot the leaflets 321, 322 of the prosthetic valve to their open positions in the aortic position, the underfaces of the two arms 303, 305 are integrally formed with curved, tapered ribs 323, 324 (FIG. 9) engageable with the leaflets such as to pivot them to their open positions.

A thread 325, received within a circumferential recess 326 in part 301 and a corresponding recess 327 in part 302, retains the two parts in their holding positions holding the prosthetic valve 4. When the prosthetic valve is to be released from the valve holder, thread 325 is severed, thereby permitting the two arms 303, 305 to collapse to a releasing position releasing the prosthetic valve. The curved tapered ribs 323, 324 formed on the undersides of the two arms 303, 305, also aid the prosthetic valve 4 to drop by gravity when the two arms are pivotted to their releasing positions by severing thread 325.

To facilitate severing thread 325, pivotal part 301 is also formed with an axial slot 331 (FIG. 8) intersecting slot 326 receiving the thread 325. In addition, part 302 is also formed with an axial slot 332 aligned with axial slot 331.

Slot 327 in part 302 does not extend completely around the outer surface of that part, but rather is formed on the inner surface of that part for a portion of its length, as shown by the broken-line section 327' in FIG. 8. Slot 326 in pivotal part 301 also includes a corresponding section (not shown) formed on the inner surface of that part, rather than on the outer surface. Thread 325 is in turn formed with two knotted ends 325a, 325b extending through openings leading from internal slot section 327' and the corresponding section of slot 326. Thus, when thread 325 is severed, the thread will be positively retained within the valve holder and will not be permitted to drop into the excised annulus.

The implement illustrated in FIG. 7 is used with the optical fiber 211 for illuminating the working site, and with the valve holder 12 for holding the prosthetic valve to be implanted, as follows:

Collar 222 is fixed to the optical fiber 211 at the location such that when the optical fiber is passed through the aligned bores in handle 11, in end section 220, and in valve holder 12, the outer tip 211a of the optical fiber will just penetrate into the interior of the valve holder but will be spaced above the prosthetic valve 4 held by the holder. The valve holder 12 is conveniently attachable to the implement by threading the lower end 220a of the handle section 220 into socket 307 of the valve holder.

The valve holder 12 would be applied to the implement with the prosthetic valve 4 attached, i.e., with arms 303, 305 of the valve holder in their operative positions holding the prosthetic valve. Arms 303, 305 are retained in this operative position by thread 325 which encircles the upper ends of the two pivotal parts 301, 302. When the prosthetic valve 4 is thus attached to the valve holder, the two arms 303, 305 assure that that the two pivotal leaflets 321, 322 of the prosthetic valve are pivotted to their open positions, so that these leaflets do not interfere with the passage of the light from optical fiber 211 to the working site.

After the sutures have thus been applied to the prosthetic valve as described above, thread 325 is severed, thereby permitting the two arms 303, 305 of the valve holder to collapse, which releases the valve. As described earlier, the two knots 325a, 325b formed in the thread 325, as well as the internal location of recess section 327' (and the corresponding section of recess 326) receiving the thread, assure that the thread, when severed, will be retained within the valve holder and will not drop into the excised annulus.

The valve holder may be made of any suitable material, transparent, translucent or opaque. Preferably, however, its outer surface is roughened so as to preclude reflection of the light towards the surgeons's eyes.

The implement illustrated in FIGS. 7–11 may be used to illuminate the intracardiac cavities, such as the right atrium, left atrium, right ventrical, left ventrical, aortic root, etc., with high intensity illumination from a very short distance, thus avoiding interference with the light, shadows, etc. Since the illumination is conducted by the light conductor (e.g., a bundle of optical fibers of about 3 mm in diameter), a minimum of heating of the working site is produced, which is a very important advantage during heart surgery. In addition, the leaflets of the prosthetic valve effectively reflect and spread the light to the working area. The illuminator also produces enhanced vision and improved exposure in deep cavities which are difficult to illuminate.

Figure 12:
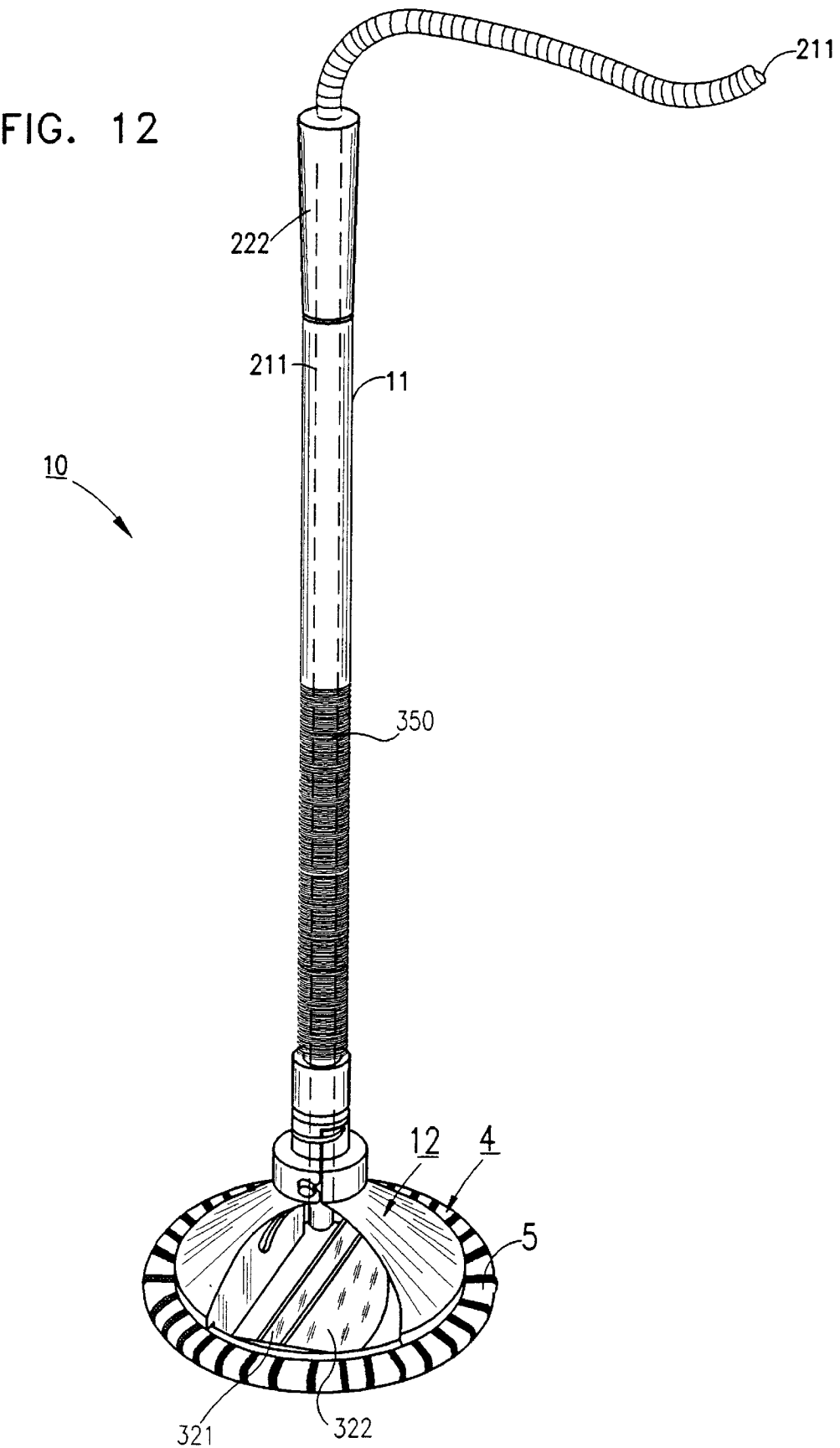
FIG. 12 illustrates an implement similar to that of FIG. 7 but without a suture retainer.

FIG. 12 illustrates an implement similar to that described above with respect to FIGS. 7–11, but without the suture retainer 15. Such an implement can therefore provide all the advantages described above for illuminating the working site, but can use other arrangements for applying the sutures.

A further feature in the implement illustrated in FIG. 12 is that its end section 220 of the handle 11, coupling the handle to the valve holder 12, includes a bendable portion, shown at 350. Portion 350 is bendable laterally of the handle axis and is retained in its bent position to facilitate manipulating the valve holder, and the prosthetic valve held thereby, with respect to the working area. Such a bendable portion 350 could be, for example, a coil or strip of plastic, metal, or plastic-coated metal, which is bendable laterally and which has memory so as to retain its bent configuration until bent to another configuration. As shown in FIG. 12, such a construction is particularly advantageous when the implement does not include a suture retainer, since bending the implement as described above would interfere with the sutures held by the retainer.

Figure 13:
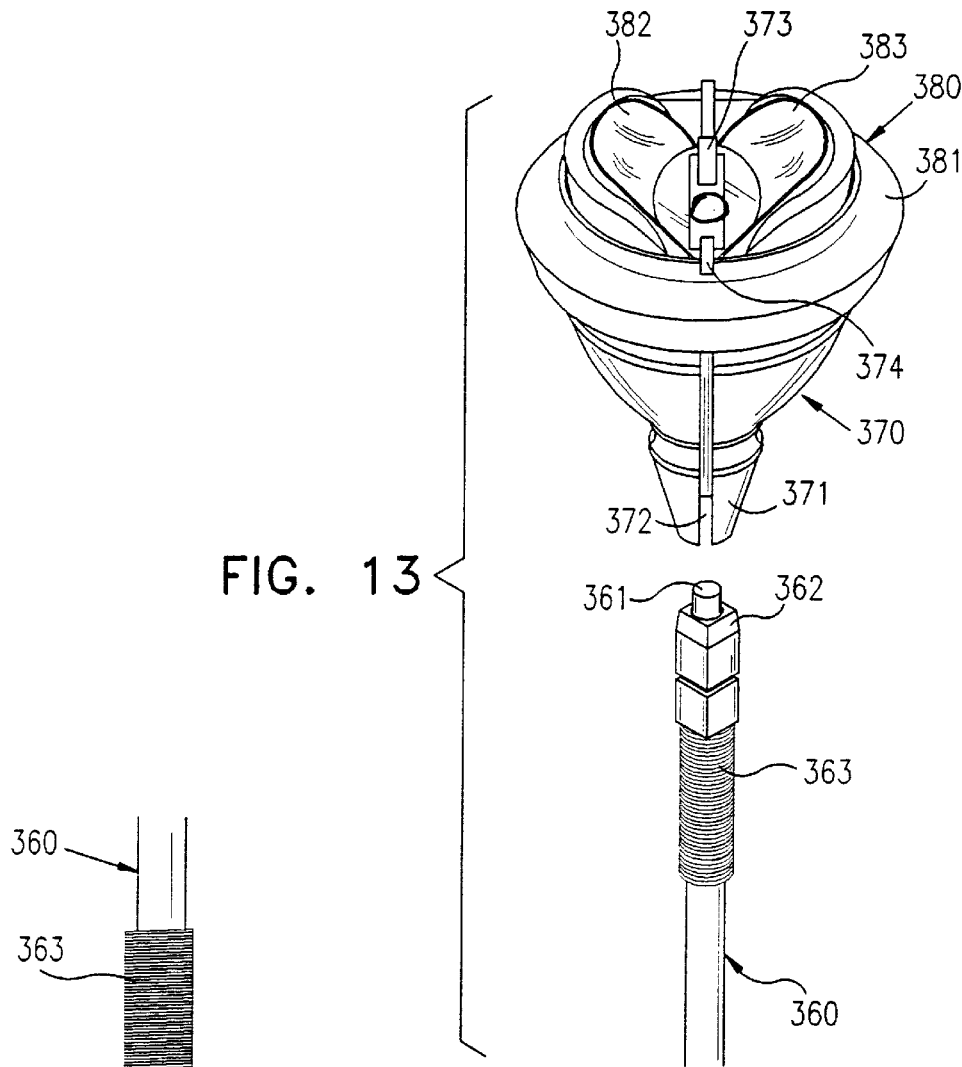
FIG. 13 is an exploded view illustrating an implement similar to that of FIG. 12 but with a valve holder for another known type of prosthetic valve.
Figure 14:
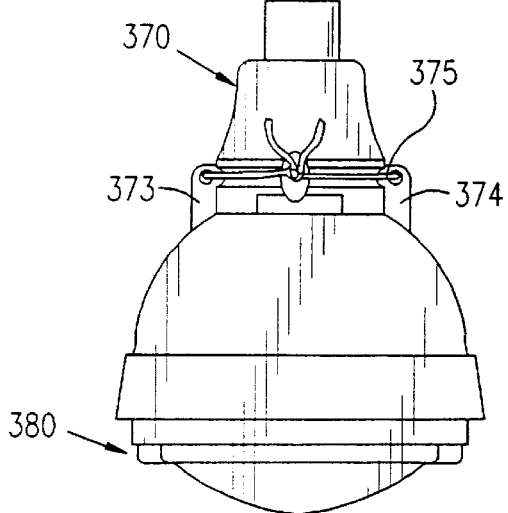
FIG. 14 is a side view of the implement of FIG. 13 in assembled condition.

FIGS. 13 and 14 illustrate an implement 360, and a valve holder 370, for releasably holding another known type of prosthetic valve 380.

Implement 360 includes a light conductor 361 extending through the implement handle for coupling to an external light source (not shown), and a square head 362 attachable by a snap fit within a socket in a collar 371 carried by the valve holder 370. Implement 360 further includes a bendable portion 363, corresponding to bendable portion 350 in the implement of FIG. 12.

When valve holder 370 is attached to the implement 360, the tip of the light conductor 361 is received within a bore 372 formed in the valve holder to conduct the light from the light conductor 361 to the working area via aligned openings in the valve holder 370 and the prosthetic valve 380 releasably held thereby. Valve holder 370 includes a pair of hooks 373, 374 which are pivotally mounted to releasably hold the prosthetic valve 380. These hooks are normally retained in their holding positions by a thread 375 (FIG. 14), which is severed to release the prosthetic valve 380.

Prosthetic valve 380 is of a commercially available type which includes a sewing ring 381 and a pair of pivotal leaflet-type valve members 382, 383. Valve holder 370 is also of a known commercial type normally supplied with prosthetic valve 380, except that in this case its collar 371, constituting its attaching section for attachment to the implement 360, is formed with bore 372 dimensioned to receive the tip of the light conductor 361. In this known type of prosthetic valve, the two leaflets 382, 383 are normally biassed to their open pivotal positions when held by the valve holder, thereby permitting the light from the light conductor 360 to pass through the valve holder and the valve to the working site.

Since valve holder 370 and the prosthetic valve 380 are otherwise of a known commercial design, further details of their construction are not set forth herein.

Figure 15:
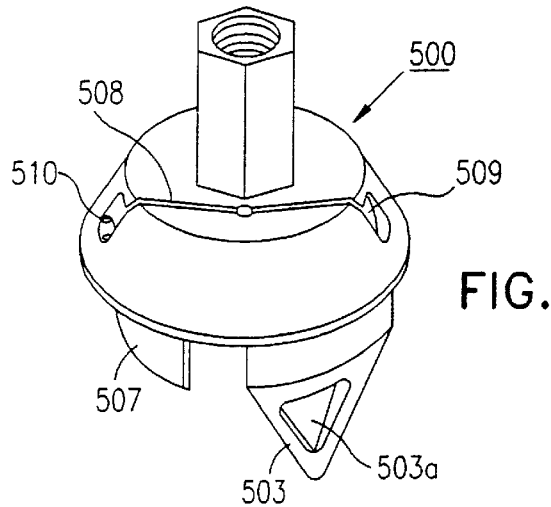
FIG. 15 is an exploded view illustrating another implement constructed in accordance with the present invention including a valve holder for another type of known prosthetic valve.
Figure 16:
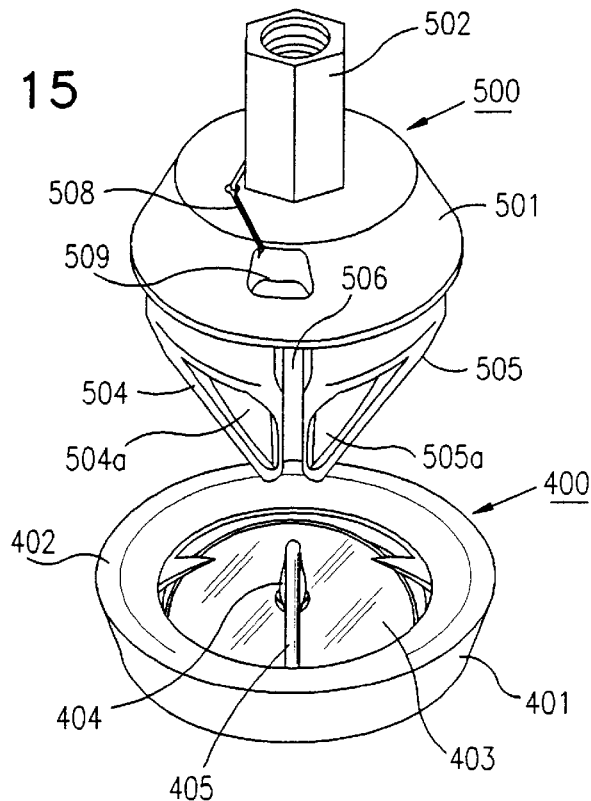
FIG. 16 illustrates only the valve holder of FIG. 15 viewed from a different side.
Figure 17:
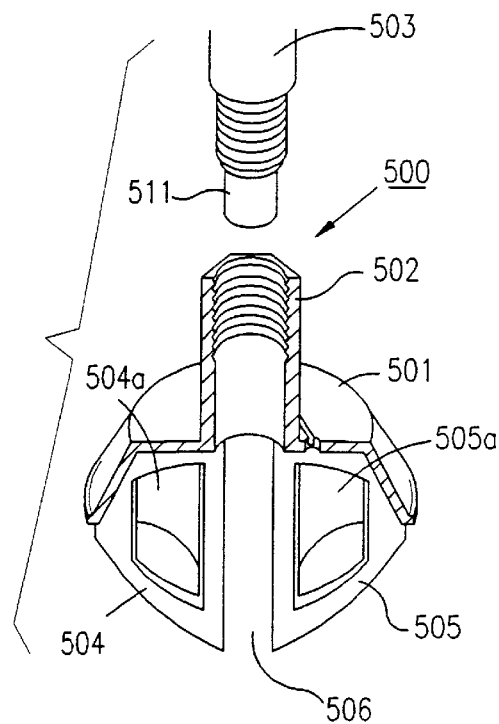
FIG. 17 is a side view of the valve holder of FIG. 16 in partial section and also illustrating the manner of its attachment to the implement.

FIGS. 15–17 illustrate the invention embodied in another known type of prosthetic valve, generally designated 400, normally supplied with another known type of valve holder, generally designated 500.

Thus, the prosthetic valve 400 includes a titanium housing 401, a sewing ring 402, and a single disc valve member 403 pivotal at its center with respect to a guide member 404 carried by a transversely-extending bar 405.

The valve holder 500 includes a housing 501 and an internally-threaded attaching section 502 for attachment to the externally-threaded end of the implement handle 503 (FIG. 17). Housing 501 of the valve holder is provided with a pair of axially-extending tapered pins or prongs 504, 505 separated by a space 506 to accommodate the transverse bar 405 of the prosthetic valve.

Thus, when the prosthetic valve 400 is held by the valve holder 500, the two pins 504, 505 are received within housing 401 straddling the transverse bar 405, with the transverse bar accommodated by the space 506 between the two pins. A rib 507 (FIG. 16) on the opposite side of the holder housing 501 engages the opposite side of the valve housing 401. The valve is held within holder 500 by a thread 508 extending through openings 509, 510 in the holder, which thread is severed by the surgeon to release the valve from the holder.

Since both the prosthetic valve 400 and the valve holder 500 are of known constructions, further details of their construction and operation are not forth herein. For example, the prosthetic heart valve 400 may be the "Hall" (T.M.) prosthetic heart valve supplied by Medtronic, Minneapolis, Minn., and the valve holder 500 may be the holder supplied with that valve. In this case, however, the valve holder 500 is modified to accommodate the light conductor 511 carried by the implement handle 503 and received within collar 502 when attaching the valve holder to the implement handle, and also by providing the two tapered pins or plugs 504, 505 with bores or passageways therethrough 504a, 505a, for conducting the light from the light conductor 511 through the prosthetic valve to the working site. When the valve is held by the holder, the two tapered pins 504, 505 retain the valve member 403 in its open position, thereby assuring passage of the light directly to the working site.

Figure 18:
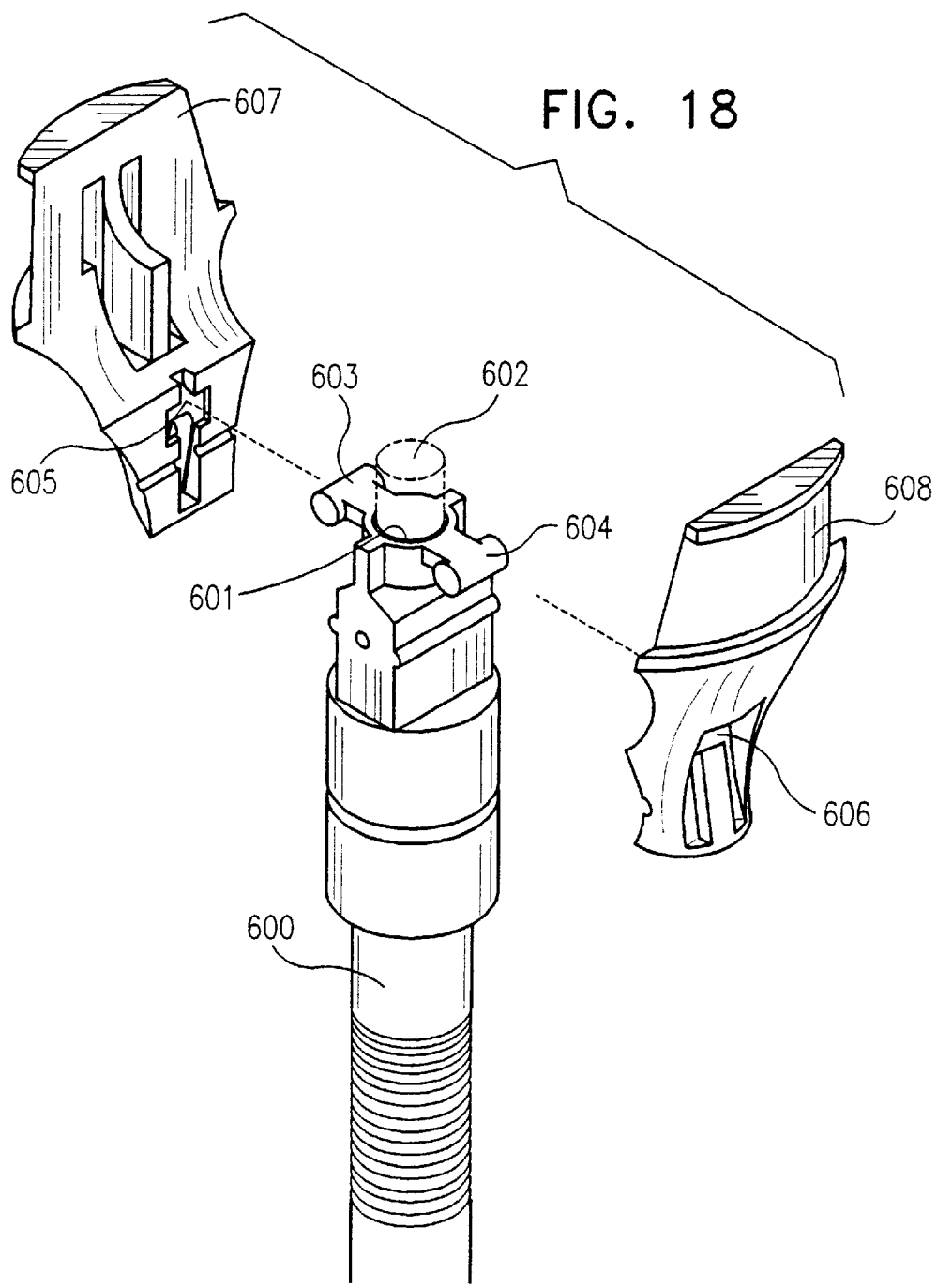
FIG. 18 is an exploded view illustrating the invention embodied in another commercially-available valve holder for holding a commercially-available prosthetic valve.

FIG. 18 illustrates a still further form of valve holder which is at present commercially available, similar to the valve holder of FIGS. 8–11 for holding a two-leaflet prosthetic valve. Thus, the implement illustrated in FIG. 18 includes a handle 600, which is normally solid. In this case, however, it is formed with a longitudinally-extending bore 601 for receiving the light conductor 602 for transmitting the light via the valve holder and the valve held thereby to the working area.

The implement illustrated in FIG. 18 is otherwise of the commercially-available construction, including a pair of trunnions 603, 604 pivotally received within socket 605, 606 formed in a pair of pivotal arms 607, 608, which arms are normally retained in a holding position by a thread (not shown) and collapse to the releasing position upon severing the thread in the same manner as in the valve holder illustrated in FIGS. 8–11.

Further variations may be made in the invention. For example, another valve holder is commercially available similar to that of FIGS. 15–17, but including four tapered pins, rather than two. It has been found that the illuminating arrangement of the present invention as illustrated in FIGS. 15–17 may also be used in that construction of valve holder with two of the tapered pins formed with the light-passage bores.

Another possible arrangement is to have the light conductor penetrate the valve holder from the side, rather than along the central axis. This may be particularly advantageous in tissue valves to avoid penetration through the cusps, and may be implemented by extending the optical fiber to one or more sides of the holder. Many other arrangements will be apparent to those skilled in the art.

While the invention has been described with respect to several preferred embodiments, it will be appreciated that these are set forth merely for purposes of example, and that many features could be used without other features. For example, the suture retainer could be used with or without the illuminator, and vice versa. In addition, the invention could be used with a fiber optic tube of the two-channel type, wherein one channel is used for illuminating the working area, and the second channel is used for imaging the working area for display or recording purposes. Also, while the invention is particularly useful for implanting prosthetic valves, it will be appreciated that other prosthetic devices could be implanted in an excised annulus in the manner and with the implement described above. Many other variations, modifications and applications of the invention will be apparent.

I claim:

1. A valve holder for holding a prosthetic valve having a sewing ring for implanting the valve in a working area, and a pivotal valve member pivotal to open and closed positions;

said valve holder including an attaching section for attaching the valve holder to a manipulatable surgical implement, and a releasble holding section for releasably holding the prosthetic valve;

said valve holder being formed with a bore extending through said attaching section and dimensioned to receive a light conductor from said surgical implement and to space the tip of the light conductor from said pivotal valve member;

said releasable holding device holding the prosthetic valve with the valve member in its open position to permit light from the light conductor to pass through the valve holder and the prosthetic valve held thereby to illuminate the working area.

2. The valve holder according to claim 1, for a prosthetic valve which includes two pivotal valve members in the form of leaflets, said releasable holding device holding the pivotal valve member with both leaflets pivotted to their open positions.

3. The valve holder according to claim 2, wherein said valve holder comprises:

a pair of arms pivotally mounted at their upper ends to assume either a holding position for holding a prosthetic valve, or a releasing position for releasing the prosthetic valve;

and a thread engaging said arms for retaining them in said holding position, but being severable to permit the arms to collapse to said releasing position;

said pair of arms being formed at their upper ends with a central axial bore for receiving said light conductor;

said upper ends of the pair of arms being pivotally mounted by a pair of hinges at diametrically opposite sides of the arms on opposite sides of said central axial bore.

4. The valve holder according to claim 3, wherein said pair of arms include lower faces formed with curved, tapered ribs engageable with the pivotal leaflet valve members of the prosthetic valve for retaining said leaflets in their open positions.

5. The valve holder according to claim 2, wherein said holding device comprises a pair of hooks pivotally mounted at opposite ends of the valve holder for releasably engaging the prosthetic valve, and a thread engaging said hooks for retaining them in a holding position with respect to the prosthetic valve, but being severable to permit the hooks to pivot to a releasing position to release the prosthetic valve.

6. The valve holder according to claim 1, wherein the prosthetic valve includes a single valve member pivotally mounted to a transversely-extending bar, said holding device comprising a pair of tapered pins spaced from each other to straddle said transverse bar and to pivot the valve member to its open position, said tapered pins also being formed with bores therethrough for conducting the light from the light conductor to said working area.

7. The combination of a valve holder according to claim 1, and a prosthetic valve releasably held by said valve holder.

8. The valve holder according to claim 1, wherein the implement includes an intermediate section between said handle and said valve holder, which intermediate section is bendable laterally of the handle axis and retains its bent position to facilitate manipulating the valve holder, and the prosthetic valve held by, with respect to the working area.

* * * * *